United States Patent
Hayward et al.

(12) 
(10) Patent No.: US 6,534,456 B2
(45) Date of Patent: Mar. 18, 2003

(54) EXTRUDABLE MULTIPHASE COMPOSITION COMPRISING A LAMELLAR PHASE AND AN ISOTROPIC PHASE

(75) Inventors: Christine Hayward, Torrington, CT (US); Rosa Paredes, Shelton, CT (US)

(73) Assignee: Unilever Home and Personal Care USA, division of Conopco, Inc., Greenwich, CT (US)

( * ) Notice: Subject to any disclaimer, the term of this patent is extended or adjusted under 35 U.S.C. 154(b) by 0 days.

(21) Appl. No.: 09/767,293

(22) Filed: Jan. 23, 2001

(65) Prior Publication Data

US 2002/0010110 A1 Jan. 24, 2002

Related U.S. Application Data

(60) Provisional application No. 60/190,779, filed on Mar. 20, 2000.

(51) Int. Cl.⁷ .................................................. A61K 7/50
(52) U.S. Cl. ........................ 510/130; 570/158; 570/159; 570/406; 424/401; 578/844
(58) Field of Search ................................. 510/122, 130, 510/158, 159, 406; 424/401; 518/844

(56) References Cited

U.S. PATENT DOCUMENTS

| | | |
|---|---|---|
| 4,335,103 A | 6/1982 | Barker et al. |
| 5,059,414 A | 10/1991 | Dallal et al. |
| 5,612,307 A | 3/1997 | Chambers et al. |
| 5,929,019 A | 7/1999 | Puvvada et al. |

FOREIGN PATENT DOCUMENTS

| | | |
|---|---|---|
| EP | 0 468 703 A1 | 1/1992 |
| WO | 90/13283 | 11/1990 |
| WO | 94/03152 | 2/1994 |
| WO | 9602229 | 2/1996 |
| WO | 9705857 | 2/1997 |
| WO | 9811871 | 3/1998 |
| WO | 98/24399 | 6/1998 |

OTHER PUBLICATIONS

PCT Search Report PCT/EP 01/02345.

*Primary Examiner*—Necholus Ogden
(74) *Attorney, Agent, or Firm*—Alan A. Bornstein

(57) ABSTRACT

The invention relates to a plurality of liquid cleansing compositions having at least one lamellar phase which possesses a lotion-like appearance conveying signals of enhanced moisturization and at least one abutting isotropic phase having enhanced cleansing ability. The inventive composition is contained in a partitionless container in one embodiment conveying signals of a plurality of compositions. This multiphase composition is stable upon storage and is dispensed as a striped product where typically one stripe has primarily a cleansing function and a second stripe has primarily a moisturization function.

17 Claims, 1 Drawing Sheet

EXTRUDABLE MULTIPHASE COMPOSITION COMPRISING A LAMELLAR PHASE AND AN ISOTROPIC PHASE

This application claims the benefit of U.S. provisional application No. 60/190,779, filed Mar. 20, 2000.

BACKGROUND

1. Field of the Invention

The present invention relates to extrudable multiphase liquid cleansing compositions of the type typically used in skin cleansing or shower gel compositions which compositions contain both "structured" lamellar and "unstructured" isotropic phase compositions.

2. Background of the Invention

Dual Phase Cleansing and Related Compositions

Compositions which both provide a cleansing function and a moisturizing benefit are known. For example, WO 90/13283 to Green, et al., published on Nov. 15, 1990; included herein by reference, discloses compositions comprising an acyl ester of an isethionic acid salt, a long chain fatty acid, a moisturizer component and optional soap.

One problem which had been previously encountered with such dual purpose compositions is that they contain an insufficient level of moisturizer component; or an insufficient amount deposits on use.

Another problem associated with such dual cleansing and moisturizing compositions is instability. According to WO 94/03152 to Helliwell, published on Feb. 17, 1994; included herein by reference, concerned with shower gels comprising a non-soap detergent, silicone oil and cationic polymers, the maximum average droplet size of the silicone oil that can be used is 2 microns, if product stability is to be maintained.

In commonly assigned U.S. Pat. No. 5,612,307 issued to Chambers, et al., on Mar. 18, 1997, included herein by reference, enhanced deposition of benefit agent was found to be obtained in a stable formulation by using a dual cleansing and moisturizing product in which the cleansing and moisturizing components were separately, but combinedly dispensed from a packaging means as discrete domains/stripes.

More specifically, the compositions of Chambers, et al. comprised a surfactant containing base formulation and a benefit agent wherein the benefit agent and base formulation were physically separate (not in direct contact) but were nonetheless dispensable from a single packaging means comprising both the base formulation and benefit agent as individual stripes. The stripes had width of at least 1000 microns and base formulation and benefit agent stripes were not post mixed prior to use (compared to EP 468,703 to Unilever where post-mixing is required).

In commonly assigned U.S. Pat. No. 5,929,019 issued to Puvvada et al., on Jul. 27, 1999; included herein by reference, the same separately dispensed, non-mixed prior to use, dual cleanser/moisturizer compositions described by Chambers, et al., is disclosed except that the benefit agent stripe had been modified so that it now may include surfactant.

Multiphase cleansing and cosmetic compositions which are not segregated in their package are also known. For example, in U.S. Pat. No. 5,059,414 issued to Dallal et al. on Oct. 22, 1991; included herein by reference, a multi-phase high viscosity cosmetic product containing two or more independent products in independent gelling matrices in single container, along with simultaneous dispensing, is described. However, Dallal describes multiphase isotropic gel products for the hair, whereas the present invention relates to a composition comprising at least one lamellar liquid and at least one isotropic liquid for personal care (hand, body and hair).

In another example, WO 9824399 to Bordat et al., published on Jun. 11, 1998; included herein by reference, describes highly viscous, separate aqueous and oil phase emulsion compositions squeezed out together as single strand from tube dispenser for use with the skin, body or hair. In comparison, the present invention uses at least one lamellar liquid and at least one isotropic liquid.

In a further example, U.S. Pat. No. 4,335,103 issued to Barker, et al., on Jun. 15, 1982: included herein by reference, describes a multiphase cosmetic composition having at least one cream or emulsion phase and one gel phase. Barker, et al., does not however disclose the stable composition of the present invention comprising at least one lamellar liquid and at least one isotropic liquid.

Lamellar Compositions

The rheological behavior of all surfactant solutions, including liquid cleansing solutions, is strongly dependent on the microstructure, i.e., the shape and concentration of micelles or other self-assembled structures in solution.

When there is sufficient surfactant to form micelles (concentrations above the critical micelle concentration or CMC), for example, spherical, cylindrical (rod-like) or discoidal micelles may form. As surfactant concentration increases, ordered liquid crystalline phases such as lamellar phase, hexagonal phase or cubic phase may form. The lamellar phase, for example, consists of alternating surfactant bilayers and water layers. These layers are not generally flat but fold to form submicron spherical onion like structures called vesicles or liposomes. The hexagonal phase, on the other hand, consists of long cylindrical micelles arranged in a hexagonal lattice. In general, the microstructure of most personal care products consist of either spherical micelles; rod micelles; or a lamellar dispersion.

As noted above, micelles may be spherical or rod-like. Formulations having spherical micelles tend to have a low viscosity and exhibit Newtonian shear behavior (i.e., viscosity stays constant as a function of shear rate; thus, if easy pouring of product is desired, the solution is less viscous and, as a consequence, it doesn't suspend as well). In these systems, the viscosity increases linearly with surfactant concentration.

Rod micellar solutions are more viscous because movement of the longer micelles is restricted. At a critical shear rate, the micelles align and the solution becomes shear thinning. Addition of salts increases the size of the rod micelles thereof increasing zero shear viscosity (i.e., viscosity when sitting in bottle) which helps suspend particles but also increases critical shear rate (point at which product becomes shear thinning; higher critical shear rates means product is more difficult to pour).

Lamellar dispersions differ from both spherical and rod-like micelles because they can have high zero shear viscosity (because of the close packed arrangement of constituent lamellar droplets), yet these solutions are very shear thinning (readily dispense on pouring). That is, the solutions can become thinner than rod micellar solutions at moderate shear rates.

In formulating liquid cleansing compositions, therefore, there is the choice of using rod-micellar solutions (whose zero shear viscosity, e.g., suspending ability, is not very good and/or are not very shear thinning); or lamellar dispersions (with higher zero shear viscosity, e.g. better suspending, and yet are very shear thinning). Such lamellar compositions are characterized by high zero shear viscosity (good for suspending and/or structuring) while simultaneously being very shear thinning such that they readily dispense in pouring. Such compositions possess a "heaping", lotion-like appearance which convey signals of enhanced moisturization.

To form such lamellar compositions, however, some compromises have to be made. First, generally higher amounts of surfactant are required to form the lamellar phase. Thus, it is often needed to add auxiliary surfactants and/or salts which are neither desirable nor needed. Second, only certain surfactants will form this phase and, therefore, the choice of surfactants is restricted.

In short, lamellar compositions are generally more desirable (especially for suspending emollient and for providing consumer aesthetics), but more expensive in that they generally require more surfactant and are more restricted in the range of surfactants that can be used.

When rod-micellar solutions are used, they also often require the use of external structurants to enhance viscosity and to suspend particles (again, because they have lower zero shear viscosity than lamellar phase solutions). For this, carbomers and clays are often used. At higher shear rates (as in product dispensing, application of product to body, or rubbing with hands), since the rod-micellar solutions are less shear thinning, the viscosity of the solution stays high and the product can be stringy and thick. Lamellar dispersion based products, having higher zero shear viscosity, can more readily suspend emollients and are typically more creamy. Again, however, they are generally more expensive to make (e.g., they are restricted as to which surfactants can be used and often require greater concentration of surfactants).

In general, lamellar phase compositions are easy to identify by their characteristic focal conic shape and oily streak texture while hexagonal phase exhibits angular fan-like texture. In contrast, micellar phases are optically isotropic.

It should be understood that lamellar phases may be formed in a wide variety of surfactant systems using a wide variety of lamellar phase "inducers" as described, for example, in U.S. Pat. No. 5,952,286 issued to Puvvada, et al., on Sep. 14, 1999. Generally, the transition from micelle to lamellar phase are functions of effective average area of headgroup of the surfactant, the length of the extended tail, and the volume of tail. Using branched surfactants or surfactants with smaller headgroups or bulky tails are also effective ways of inducing transitions from rod micellar to lamellar.

One way of characterizing lamellar dispersions include measuring viscosity at low shear rate (using for example a Stress Rheometer) when additional inducer (e.g., oleic acid or isostearic acid) is used. At higher amounts of inducer, the low shear viscosity will significantly increase.

Another way of measuring lamellar dispersions is using freeze fracture electron microscopy. Micrographs generally will show lamellar microstructure and close packed organization of the lamellar droplets (generally in size range of about 2 microns).

Isotropic Compositions

In contrast to lamellar surfactant solutions described above, single phase isotropic surfactant solutions are composed of completely miscible components whose microstructure does not vary with distance or direction in the solution. Upon comparison of the lamellar and isotropic compositions, it is found that lamellar structures do not lather as well as isotropic structures and isotropic structures do not deposit skin care ingredients in the same manner as lamellar structures. By having the two product types separated but dispensed simultaneously, the lather benefit of the isotropic phase and the deposition of the lamellar is advantageously combined.

SUMMARY OF THE INVENTION

Applicants have discovered that a stable, extrudable multiphase product can be prepared having at least one lamellar phase and at least one isotropic phase. The term multiphase product is here defined as the combination of at least one lamellar composition having a viscosity of at least about 80,000 cps (T-bar) at 25° C., and at least one isotropic composition having a viscosity of at least about 15,000 cps (cone and plate) at 25° C. Preferably the viscosity of the lamellar and the isotropic compositions have an upper limit of 300,000 cps and 100,000 cps respectively at 25° C. in order to facilitate filling containers and dispensing with a conventional pump bottle. The lamellar and isotropic phases may have substantially the same or different compositions. Preferably the lamellar and isotropic phases are rheologically compatible, i.e. they have the same flow properties under the conditions of filling, storage, and product usage.

The lamellar and isotropic phases preferably have different colors or other visual differences and preferably are filled vertically or in a pulsating manner in a single container without any partitions, i.e. "partitionless".

Squeezing a flexible container holding the inventive product may dispense the product but a single pump, or the like, is preferably used to dispense the product. When dispensed, each phase of the multiphase inventive product should be present in the concentration range of 1–99 weight %. In this manner, duality in the case of a two phase system, can be advantageously, economically, and visually communicated through a single, partitionless container. Another advantage of the inventive product is the fact that separate lamellar and isotropic compositions having specific functions, e.g. cleansing and moisturizing the skin may be simultaneously dispensed in a partitionless container. A further advantage of using at least one lamellar composition is that elevated amounts of emollients can be added to the formula without affecting product stability. Unexpectedly, the lamellar and isotropic phases in the inventive product remain separated (i.e. do not mix) at room temperature for at least 70 days and at elevated temperature (50° C.) for at least one week. "Stability" is therefore defined as used herein as the ability of the multiphase lamellar-isotropic product to maintain the separation of each phase from the other under such combination of time and temperature.

In accordance with these and other aspects of the invention, the invention will now be described with reference to the accompanying drawing.

DETAILED DESCRIPTION OF THE INVENTION

Figure 1:
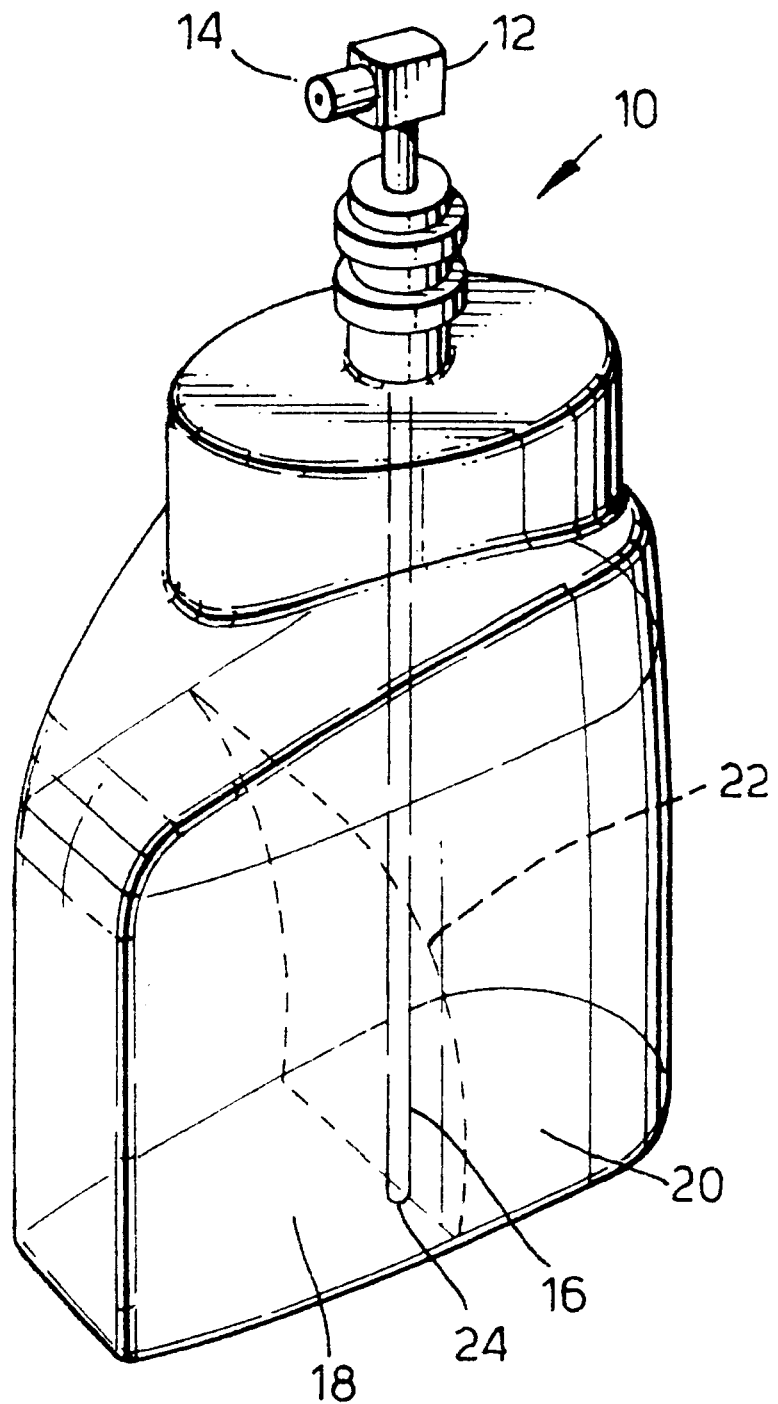
FIG. 1 is a perspective view showing one embodiment of the present invention where two separate liquid cleansing compositions, one in lamellar phase, and the other in isotropic phase are contained in a partitionless container.

Referring to FIG. 1, partitionless container 10 contains two separate liquid cleansing compositions 18 and 20 separated by boundary layer 22. Also depicted in FIG. 1 is pump mechanism 12 having a single outlet 14 and suction tube 16 with a single intake hole 24. Preferably cleansing compositions 18 and 20 are visually distinct signaling duality to the consumer and are in the form of a lamellar phase and an isotropic phase respectively. More preferably cleansing compositions 18 and 20 have different colors or distinctive visual clarity. In another embodiment of the invention, the partitionless container may contain more than two separate liquid cleaning compositions as long as at least one composition is present as a lamellar phase and at least one composition is present as an isotropic phase and there is at least one interface between the two phases.

The present invention also relates to multiphase liquid cleansing compositions, wherein the liquid contains both a lamellar and an isotropic phase component, comprising a surfactant system, preferably a system which contains at least about 5 weight percent, preferably at least about 10 weight percent of surface active compounds. The inventive composition also includes an amphoteric and/or zwitterionic surfactant. Preferably the amphoteric or zwitterionic surfactant, or a blend thereof is present at about 2 to 40 weight percent, preferably at about 3 to 20 weight percent. The inventive composition also contains at least one anionic surfactant. Preferably the anionic surfactant is present at about 3 to 40 weight percent, more preferably at about 5 to 20 weight percent and more preferably at about 3 to 10 weight percent. The inventive composition also contains a lamellar structurant. Preferably the lamellar structurant is present at about 0.3 to 15 weight percent, more preferably at about 0.5 to 5 weight percent.

The lamellar component phase of the inventive multiphase lamellar-isotropic composition preferably has a low shear viscosity in the range of about 80,000 to 300,000 centipoises (cps) measured at 0.5 RPM using T-bar spindle A using the procedure described below. More preferably the viscosity range is 100,000 to 200,000 cps.

The isotropic component phase of the inventive multiphase lamellar-isotropic composition preferably has a viscosity in the range of about 15,000 to 100,000 centipoises (cps) measured at 0.5 RPM using a Brookfield Cone and Plate viscometer with spindle number S41. More preferably the viscosity range is 15,000 to 50,000 cps and the abutting lamellar and isotropic phases are rheologically compatible.

Surfactants

The surfactant system of the subject invention comprises 5 to 60% by weight, preferably 10 to 30% by wt. of the total composition and comprises:

(a) at least one anionic surfactant;

(b) At least one amphoteric and/or zwitterionic surfactant;

(c) At least one lamellar structurant compound; and (d) optionally one or more nonionic surfactants, cationic surfactants, or blends thereof.

The anionic surfactant (which may comprise 3 to 40% by wt. of total composition) may be, for example, an aliphatic sulfonate, such as a primary alkane (e.g., $C_8$–$C_{22}$) sulfonate, primary alkane (e.g., $C_8$–$C_{22}$) disulfonate, $C_8$–$C_{22}$ alkene sulfonate, $C_8$–$C_{22}$ hydroxyalkane sulfonate or alkyl glyceryl ether sulfonate (AGS); or an aromatic sulfonate such as alkyl benzene sulfonate, and the like.

The anionic may also be an alkyl sulfate (e.g., $C_{12}$–$C_{18}$ alkyl sulfate) or alkyl ether sulfate (including alkyl glyceryl ether sulfates), and the like. Among the alkyl ether sulfates are those having the formula:

$RO(CH_2CH_2O)_nSO_3M$ wherein R is an alkyl or alkenyl having 8 to 18 carbons, preferably 12 to 18 carbons, n has an average value of greater than 1.0, preferably between 2 and 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$–$C_{22}$ sulfosuccinates); alkyl and acyl taurates, alkyl and acyl sarcosinates, sulfoacetates, $C_8$–$C_{22}$ alkyl phosphates and phosphates, alkyl phosphate esters and alkoxyl alkyl phosphate esters, acyl lactates, $C_8$–$C_{22}$ monoalkyl succinates and maleates, sulphoacetates, and acyl isethionates, and the like.

Sulfosuccinates may be monoalkyl sulfosuccinates having the formula:

$R^4O_2CCH_2CH(SO_3M)CO_2M$;

amido-MEA sulfosuccinates of the formula $R^4CONHCH_2CH_2O_2CCH_2CH(SO_3M)CO_2M$ wherein $R^4$ ranges from $C_8$–$C_{22}$ alkyl and M is a solubilizing cation;

amido-MIPA sulfosuccinates of formula $RCONH(CH_2)CH(CH_3)(SO_3M)CO_2M$ where M is as defined above.

Also included are the alkoxylated citrate sulfosuccinates; and alkoxylated sulfosuccinates such as the following:

$$R-O-(CH_2CH_2O)_n\overset{O}{\overset{\|}{C}}CH_2CH(SO_3M)CO_2M$$

wherein n=1 to 20; and M is as defined above.

Sarcosinates are generally indicated by the formula $RCON(CH_3)CH_2CO_2M$, wherein R ranges from $C_8$ to $C_{20}$ alkyl and M is a solubilizing cation.

Taurates are generally identified by formula $R^2CONR^3CH_2CH_2SO_3M$ wherein $R^2$ ranges from $C_8$–$C_{20}$ alkyl, $R^3$ ranges from $C_1$–$C_4$ alkyl and M is a solubilizing cation.

Another class of anionics are carboxylates such as follows:

$R-(CH_2CH_2O)_nCO_2M$ wherein R is $C_8$ to $C_{20}$ alkyl; n is 0 to 20; and M is as defined above.

Another carboxylate which can be used is amido alkyl polypeptide carboxylates such as, for example, Monteine LCQ® by Seppic.

Another surfactant which may be used are the $C_8$–$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

Acyl isethionates, when present, will generally range from about 0.5–15% by weight of the total composition. Preferably, this component is present from about 1 to about 10%.

The acyl isethionate may be an alkoxylated isethionate such as is described in U.S. Pat. No. 5,393,466, Titled "Fatty Acid Esters Of Polyalkoxylated Isethionic Acid" issued Feb. 28, 1995 to liardi et al., hereby incorporated by reference into the subject application. This compound has the general formula:

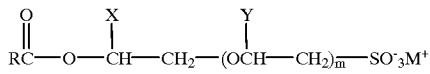

wherein R is an alkyl group having 8 to 18 carbons, m is an integer from 1 to 4, X and Y are hydrogen or an alkyl group having 1 to 4 carbons and $M^+$ is a monovalent cation such as, for example, sodium, potassium or ammonium.

Zwitterionic and Amphoteric Surfactants

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for these compounds is:

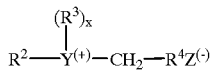

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Examples of such surfactants include:

4-[N,N-di(2-hydroxyethyl)-N-octadecylammonio]-butane-1-carboxylate;
5-[S-3-hydroxypropyl-S-hexadecylsulfonio]-3-hydroxypentane-1-sulfate;
3-[P,P-diethyl-P-3,6,9-trioxatetradexocylphosphonio]-2-hydroxypropane-1-phosphate;
3-[N,N-dipropyl-N-3-dodecoxy-2-hydroxypropylammonio]-propane-1-phosphonate;
3-(N,N-dimethyl-N-hexadecylammonio)propane-1-sulfonate;
3-(N,N-dimethyl-N-hexadecylammonio)-2-hydroxypropane-1-sulfonate;
4-[N,N-di(2-hydroxyethyl)-N-(2-hydroxydodecyl) ammonio]-butane-1-carboxylate;
3-[S-ethyl-S-(3-dodecoxy-2-hydroxypropyl)sulfonio]-propane-1-phosphate;
3-[P,P-dimethyl-P-dodecylphosphonio]-propane-1-phosphonate; and
5-[N,N-di(3-hydroxypropyl)-N-hexadecylammonio]-2-hydroxy-pentane-1-sulfate.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

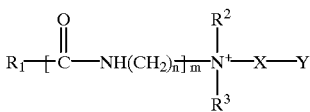

where
$R^1$ is alkyl or alkenyl of 7 to 18 carbon atoms;
$R^2$ and $R^3$ are each independently alkyl, hydroxyalkyl or carboxyalkyl of 1 to 3 carbon atoms;
n is 2 to 4;
m is 0 to 1;
X is alkylene of 1 to 3 carbon atoms optionally substituted with hydroxyl, and
Y is —$CO_2$— or —$SO_3$—

Suitable amphoteric detergents within the above general formula include simple betaines of formula:

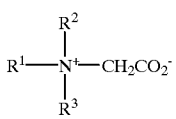

and amido betaines of formula:

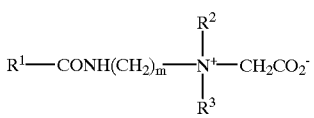

where m is 2 or 3.

In both formulae $R^1$, $R^2$ and $R^3$ are as defined previously. $R^1$ may in particular be a mixture of $C_{12}$ and $C_{14}$ alkyl groups derived from coconut so that at least half, preferably at least three quarters of the groups $R^1$ have 10 to 14 carbon atoms. $R^2$ and $R^3$ are preferably methyl. A suitable betaine is cocoamidopropyl betaine.

A further possibility is that the amphoteric detergent is a sulphobetaine of formula

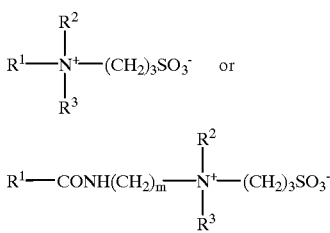

where m is 2 or 3, or variants of these in which —$(CH_2)_3$ $SO^-_3$ is replaced by

In these formulae $R^1$, $R^2$ and $R^3$ are as discussed previously.

Amphoacetates and diamphoacetates are also intended to be covered in possible zwitterionic and/or amphoteric compounds which may be used, especially C8–C20 amphoacetates or mixtures thereof, and the like. A suitable amphoacetate is sodium laurylamphoacetate.

The amphoteric/zwitterionic surfactant, when used, generally comprises 2 to 30%, preferably 3 to 20% by weight, more preferably 3 to 10% of the composition.

A preferred surfactant system of the invention comprises the following: anionic surfactant (e.g. alkali metal alkyl ethersulfate), 2–50%; amphoteric surfactant (e.g. alkyl betaine or alkyl amphoacetate), 3–20%.

The surfactant system may also optionally comprise a nonionic surfactant.

The nonionic which may be used includes in particular the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are alkyl ($C_6$–$C_{22}$) phenols-ethylene oxide condensates, the condensation products of aliphatic ($C_8$–$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides, and the like.

The nonionic may also be a sugar amide, such as a polysaccharide amide. Specifically, the surfactant may be one of the lactobionamides described in U.S. Pat. No. 5,389,279 titled "Compositions comprising nonionic glycolipid surfactants" issued on Feb. 14, 1995 to Au et al. which is hereby incorporated by reference or it may be one of the sugar amides described in U.S. Pat. No. 5,009,814 titled "Use of n-polyhydroxyalkyl fatty acid amides as thickening agents for liquid aqueous surfactant systems" issued on Apr. 23, 1991 to Kelkenberg, hereby incorporated into the subject application by reference.

Other surfactants which may be used are described in U.S. Pat. No. 3,723,325 to Parran Jr. and alkyl polysaccharide nonionic surfactants as disclosed in U.S. Pat. No. 4,565,647 titled "Foaming surfactant compositions", issued on Jan. 21, 1986 to Llenado, both of which are also incorporated into the subject application by reference.

Preferred alkyl polysaccharides are alkylpolyglycosides of the formula

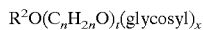

$$R^2O(C_nH_{2n}O)_t(\text{glycosyl})_x$$

wherein $R^2$ is selected from the group consisting of alkyl, alkylphenyl, hydroxyalkyl, hydroxyalkylphenyl, and mixtures thereof in which alkyl groups contain from about 10 to about 18, preferably from about 12 to about 14, carbon atoms; n is 0 to 3, preferably 2; t is from 0 to about 10, preferably 0; and x is from 1.3 to about 10, preferably from 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominantly the 2-position.

The nonionic comprises 0 to 40% by wt. in each phase of the composition, preferably 0 to 10% by wt.

Lamellar Structurant

The compositions of the invention utilize about 0.3% to 15% by wt., preferably 0.5 to 5% by wt. of a structuring agent which functions in the lamellar compositions to form a lamellar phase. Such lamellar phase enables its composition to suspend particles more readily (e.g., emollient particles) while still maintaining good shear thinning properties. The lamellar phase also provides consumers with desired rheology ("heaping").

The structurant is preferably a fatty acid or ester derivative thereof, a fatty alcohol, or trihydroxystearin, and the like. More preferably the structurant is selected from the group consisting of lauric or isostearic acid, or trihydroxystearin.

Examples of fatty acids which may be used are $C_{10}$–$C_{22}$ acids such as the following: lauric acid, oleic acid, isostearic acid, linoleic acid, linolenic acid, ricinoleic acid, elaidic acid, arichidonic acid, myristoleic acid and palmitoleic acid, and the like. Ester derivatives include propylene glycol isostearate, propylene glycol oleate, glyceryl isostearate, glyceryl oleate and polyglyceryl diisostearate, and the like.

Oil/Emollient

One of the principle benefits of the invention is the ability to suspend oil/emollient particles in one or more lamellar phases in the multiphase composition. The following oil/emollients may optionally be suspended in the compositions of the invention.

Various classes of oils are set forth below.

Vegetable oils: Arachis oil, castor oil, cocoa butter, coconut oil, corn oil, cotton seed oil, olive oil, palm kernel oil, rapeseed oil, safflower seed oil, sesame seed oil and soybean oil, and the like.

Esters: Butyl myristate, cetyl palmitate, decyloleate, glyceryl laurate, glyceryl ricinoleate, glyceryl stearate, glyceryl isostearate, hexyl laurate, isobutyl palmitate, isocetyl stearate, isopropyl isostearate, isopropyl laurate, isopropyl linoleate, isopropyl myristate, isopropyl palmitate, isopropyl stearate, propylene glycol monolaurate, propylene glycol ricinoleate, propylene glycol stearate, and propylene glycol isostearate, and the like.

Animal Fats: acetylated lanolin alcohols, lanolin, lard, mink oil and tallow, and the like.

Other examples of oil/emollients include mineral oil, petrolatum, silicone oil such as dimethyl polysiloxane, lauryl and myristyl lactate, fatty acid oils, triglycerides, glycerin, and the like.

The emollient/oil is generally used in an amount from about 0 to 70%, preferably 5 to 40% by wt. of the phase in which it is found in. Generally, it should comprise no more than 70% of such phase. A portion of the emollient may be present in the form of solid or semi-solid beads. The beads are used in an amount from about 0 to 10%, preferably 0 to 5%.

In addition, the multiphase lamellar compositions of the invention may include optional ingredients as follows:

Organic solvents, such as ethanol; auxiliary thickeners, sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer); all of which are useful in enhancing the appearance or cosmetic properties of the product.

The compositions may further comprise antimicrobials such as 2-hydroxy-4,2'4'trichlorodiphenylether (DP300); preservatives such as dimethyloldimethylhydantoin (Glydant XL1000), parabens, sorbic acid etc.

The compositions may also comprise coconut acyl mono- or diethanol amides and the like as suds boosters.

Antioxidants such as, for example, butylated hydroxytoluene (BHT) may be used advantageously in amounts of about 0.01% or higher if appropriate.

Cationic conditioners which may be used include Polyquaternium-10, Quatrisoft LM-200, Polyquaternium-24, Merquat Plus 3330, Polyquaternium 39, Ucare polymer JR400, and Jaguar® type conditioners.

Another optional ingredient which may be added are the deflocculating polymers such as are taught in U.S. Pat. No. 5,147,576 titled "Liquid Detergent Composition In The Form Of Lamellar Droplets Containing A Deflocculating Polymer", issued on Sep. 15, 1992 to Montague, hereby incorporated by reference.

Other ingredients which may be included are exfoliants such as polyoxyethylene beads, walnut sheets and apricot seeds, and the like. PH and viscosity adjusters may be used such as citric acid, glycolic acid, lactic acid, other alpha or beta hydroxy acids, and the like.

The multiphase compositions of the invention, as noted, contain both lamellar and isotropic compositions. In particular, the lamellar phase comprises 20 to 80%, preferably 30 to 65% of the total phase volume of the lamellar phase. The phase volume may be measured, for example, by conductivity measurements or other measurements which are well known to those skilled in the art. While not wishing to be bound by theory, higher phase volume is believed to provide better suspension of emollients in the lamellar phase.

The invention will now be described in greater detail by way of the following non-limiting examples. The examples are for illustrative purposes only and not intended to limit the invention in any way.

Except in the examples, or where otherwise explicitly indicated, all numbers in this description indicating amounts or ratios of materials or conditions or reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

All percentages in the specification and examples are intended to be by weight unless stated otherwise.

Example 1 is a comparative composition having a single lamellar and a single isotropic phase, as described in Table 1. The cone and plate viscosity of the isotropic phase was 14,000 cps and the T-bar viscosity of the lamellar phase was 80,000 cps (25° C.). The composition was found to degrade after one week at 25° C. resulting in the mixing of the phases. The composition was held in a transparent PET container as depicted in FIG. 1.

TABLE 1

Comparative Product

| Chemical or INCI Name | Active % in Formulation |
|---|---|
| Isotropic Side (viscosity 14,000 cps) | |
| Sodium Laureth Sulfate | 11.00 |
| Cocamidopropyl Betaine | 3.00 |
| Dimethicone Copolyol Sulfosuccinate | 0.50 |
| Hydroxypropyl Guar Hydroxypropyl Trimonium Chloride | 0.10 |
| Propylene Glycol | 0.50 |
| Acrylates Copolymer (suspension) | 3.00 |
| Acrylates/Stereath-20 Methacrylate Copolymer | 0.50 |
| DMDM Hydantoin + Iodopropyl Butylcarbamate | 0.11 |
| Sodium Hydroxide | 0.60 |
| WATER | q.s. 100 |

TABLE 1-continued

Comparative Product

| Chemical or INCI Name | Active % in Formulation |
|---|---|
| Lamellar Side (viscosity 80,000 cps) | |
| Sodium Lauroamphoacetate | 13.50 |
| Sodium Laureth Sulfate | 9.00 |
| Lauric Acid | 1.90 |
| Sunflower Seed oil | 15.00 |
| Glycerin | 2.00 |
| Guar Hydroxypropyl trimonium chloride | 0.50 |
| Citric Acid | 1.70 |
| Titanium Dioxide | 0.10 |
| DMDM Hydantoin + Iodopropynyl Butylcarbamate | 0.20 |
| EDTA | 0.02 |
| EHDP (Etidronic Acid) | 0.02 |
| Perfume | 1.00 |
| WATER | q.s. 100 |

Example 2 is an inventive composition having a single lamellar and a single isotropic phase, as described in Table 2. The cone and plate viscosity of the isotropic phase was 25,000 cps and the T-bar viscosity of the lamellar phase was 118,400 cps (25° C.). No mixing of the composition's separate phases was observed after 70 days at 25° C. in one container and after 7 days at 50° C. in a second container. The composition was held in transparent PET containers as depicted in FIG. 1.

TABLE 2

Inventive Product

| Chemical or INCI Name | Active % in Formulation |
|---|---|
| Isotropic Side (viscosity 25,000 cps) | |
| Sodium Laureth Sulfate | 11.00 |
| Cocamidopropyl Betaine | 3.00 |
| Acrylates/C12–24 Acrylate Copolymer | 0.50 |
| DMDM Hydantoin + Iodopropyl Butylcarbamate | 0.22 |
| Sodium Hydroxide | 0.60 |
| WATER | q.s. 100 |
| Lamellar Side (viscosity 118,000 cps) | |
| Sodium Lauroamphoacetate | 5.00 |
| Sodium Laureth Sulfate | 10.00 |
| Cocamide MEA | 2.00 |
| Lauric Acid | 2.80 |
| Sunflower Seed oil | 5.00 |
| Crodalan LA | 1.00 |
| Glycerin | 2.00 |
| Guar Hydroxypropyl trimonium chloride | 0.50 |
| Citric Acid | 1.00 |
| DMDM Hydantoin + Iodopropynyl Butylcarbamate | 0.22 |
| EDTA | 0.02 |
| EHP (Etidronic Acid) | 0.02 |
| Perfume | 1.00 |
| WATER | q.s. 100 |

Example 3 is an inventive composition having a single lamellar and a single isotropic phase, as described in Table 3. The cone and plate viscosity of the isotropic phase was 15,000 cps and the T-bar viscosity of the lamellar phase was 118,400 cps (25° C.). No mixing of the composition's separate phases was observed after 70 days at 25° C. in one container and after 7 days at 50° C. in a second container. The composition was held in transparent PET containers as depicted in FIG. 1.

TABLE 3

Inventive Product

| Chemical or INCI Name | Active % in Formulation |
|---|---|
| Isotropic Side (viscosity 15,000 cps) | |
| Sodium Laureth Sulfate | 11.00 |
| Cocamidopropyl Betaine | 3.00 |
| Dimethicone Copolyol Sulfosuccinate | 0.50 |
| Hydroxypropyl Guar Hydroxypropyl trimonium chloride | 0.10 |
| Propylene Glycol | 0.50 |
| Acrylates Copolymer (suspension) | 3.00 |
| Acrylates/Steareth-20 methacrylate copolymer | 0.50 |
| DMDM Hydantoin + Iodopropyl Butylcarbamate | 0.22 |
| Sodium Hydroxide | 0.60 |
| WATER | q.s. 100 |
| Lamellar Side (viscosity 118,000 cps) | |
| Sodium Lauroamphoacetate | 5.00 |
| Sodium Laureth Sulfate | 10.00 |
| Cocamide MEA | 2.00 |
| Lauric Acid | 2.80 |
| Sunflower Seed oil | 5.00 |
| Crodalan LA | 1.00 |
| Glycerin | 2.00 |
| Guar Hydroxypropyl trimonium chloride | 0.50 |
| Citric Acid | 1.00 |
| DMDM Hydantoin + Iodopropynyl Butylcarbamate | 0.22 |
| EDTA | 0.02 |
| EHP (Etidronic Acid) | 0.02 |
| Perfume | 1.00 |
| WATER | q.s. 100 |

Viscosity measurements are made in accordance with the following protocols:

T-bar Viscosity Measurement

Scope:

This method covers the measurement of the viscosity of the lamellar phase composition.

Apparatus:

Brookfield RVT Viscometer with Helipath Accessory;

Chuck, weight and closer assembly for T-bar attachment;

T-bar Spindle A;

Plastic cups diameter greater than 2.5 inches.

Procedure:

1. Verify that the viscometer and the helipath stand are level by referring to the bubble levels on the back of the instrument.
2. connect the chuck/closer/weight assembly to the Viscometer (Note the left-hand coupling threads).
3. Clean Spindle A with deionized water and pat dry with a Kimwipe sheet. Slide the spindle in the closer and tighten.
4. Set the rotational speed at 0.5 RPM. In case of a digital viscometer (DV) select the % mode and press autozero with the motor switch on.
5. Place the product in a plastic cup with inner diameter of greater than 2.5 inches. The height of the product in the cup should be at least 3 inches. The temperature of the product should be 25° C.
6. Lower the spindle into the product (~¼ inches). Set the adjustable stops of the helipath stand so that the spindle does not touch the bottom of the plastic cup or come out of the sample.
7. Start the viscometer and allow the dial to make one or two revolutions before turning on the Helipath stand. Note the dial reading as the helipath stand passes the middle of its downward traverse.
8. Multiply the dial reading by a factor of 4,000 and report the viscosity reading in cps.

Cone and Plate Viscosity Measurement

Scope:

This method covers the measurement of the viscosity of the isotropic phase composition.

Apparatus:

Brookfield Cone and Plate DV-II+Viscometer:;

Spindle S41;

Plastic cups diameter greater than 2.5 inches.

Procedure:

1. Turn on Water Bath attached to the sample cup of the viscometer. Make sure that it is set for 25° C. Allow temperature readout to stabilize at 25° C. before proceeding.
2. With the power to the viscometer off, remove the spindle (S41) by turning counterclockwise.
3. Turn the power on and press any key as requested to autozero the viscometer.
4. When the autozero function is complete, replace the spindle (turning clockwise) and press any key.
5. Attach the sample cup. Using the up/down arrow keys, slowly change the speed to 10 rpm and press the SET SPEED key. Use the SELECT DISPLAY key so that the display is in % mode.
6. Turn the motor on. If the display jumps to 0.4% or higher or will not settle to 0±0.1%, turn the adjustment ring clockwise until it does.
7. Rotate the adjustment ring counterclockwise until the reading is fluctuating between 0.0 and 1.0%. The fluctuation must occur approximately every 6 seconds.
8. Turn the adjustment ring clockwise exactly the width of one division from the setting reached in step 7.
9. Turn the motor off. Using the up/down arrow keys, slowly change the speed to 0.5 rpm and press the SET SPEED key. Use the SELECT DISPLAY so that the display is in cP.
10. Place 2±0.1 g of product to be measured into the sample cup. Attach the cup to the viscometer.
11. Allow the product to remain in the cup with the motor OFF for 2 minutes.
12. Turn the motor ON and allow the spindle to turn for 2 minutes before noting the reading on the display.

While this invention has been described with respect to particular embodiments thereof, it is apparent that numerous other forms and modifications of the invention will be obvious to those skilled in the art. The appended claims and this invention generally should be construed to cover all such obvious forms and modifications which are within the true spirit and scope of the present invention.

We claim:

1. A packaged product of a stable, extrudable, multiphase liquid cleansing composition, comprising:

at least one aqueous lamellar structured phase and at least one isotropic phase which abuts said at least one lamellar phase;

a surfactant selected from the group consisting of amphoteric, zwitterionic, or a mixture thereof;

an anionic surfactant in the concentration range of about 3 to 40 wt. % in each of said lamellar and said isotropic phase;

a lamellar structurant present in said lamellar phase of said liquid composition, selected from the group consisting of fatty acids, fatty esters, or trihydroxystearin, wherein said lamellar phase contains about 5% to 70% by wt. of oil/emollient particles and wherein said isotropic phase contains at least about 3% by wt. of surface active material;

each of said lamellar phases having a low shear viscosity value above about 80 K cps at 25° C.; and each of said isotropic phases having a low shear viscosity value above about 15 K cps at 25° C.

2. The product of claim 1 wherein each of said lamellar phases has a low shear viscosity value not exceeding about 300 K cps at 25° C.; and each of said isotropic phases has a low shear viscosity value not exceeding about 100 K cps at 25° C.

3. The product of claim 1 wherein the amphoteric surfactant concentration in each phase is in the range of about 2 to 40 weight percent.

4. The product of claim 1 further comprising a nonionic surfactant concentration in each phase is in the range of about 0 to 40 weight percent.

5. The product of claim 1 wherein the lamellar structurant concentration in the lamellar phase is in the range of about 0.3 to 15 weight percent.

6. The product of claim 1 wherein the amphoteric or zwitterionic surfactant in each phase is selected from either cocamidopropyl betaine, or an alkali metal salt of alkyl amphoacetate.

7. The product of claim 1 wherein the anionic surfactant is selected from the group consisting of alkali metal or ammonium alkyl ether sulfate, alkali metal or ammonium alkyl sarcosinate, alkali metal or ammonium alkyl sulfosuccinate, and alkali metal or ammonium alkyl sulfate.

8. The product of claim 1 wherein mixing of said abutting phases is prevented across the interfacial boundary surfaces of said abutting phases, when said composition is stored for at least 25° C. for 70 days or at least 50° C. for 7 days.

9. The product of claim 1 wherein the lamellar structurant is selected from the group consisting of lauric acid, isostearic acid, trihydroxystearin, palm kernel acid, capric acid, oleic acid, and caprylic acid; and wherein the gel forming structurant is selected from the group consisting of acrylic acid polymers, acrylates, methacrylate copolymers, acrylate methacrylate copolymers, cellulosic polymers, polyvinyl pyrrolidone, polysaccharides, silica, petrolatum, glycols, soaps and salts.

10. A packaged product of an extrudable aqueous, multiphase, structured liquid composition, comprising:

at least one aqueous lamellar structured phase and at least one isotropic phase which abuts said at least one lamellar phase;

at least 5 weight percent of surface active material in each of said lamellar and isotropic phase;

at least about 5 weight percent of oil/emollient particles in said lamellar phase;

about 2 to 30 weight percent of one or more amphoteric, or zwiterionic surfactants or a blend thereof in each of said lamellar and isotropic phase;

about 2 to 40 weight percent of an anionic surfactant in each of said lamellar and isotropic phase;

about 0.5 to 10 weight percent of a lamellar structurant selected from the group consisting of fatty acids, fatty esters, or trihydroxystearin in each said lamellar phase;

each of said lamellar phases having a low shear viscosity value between 80 and 300 K cps at 25° C.; and each of said isotropic phases having a low shear viscosity value between 15 and 100 K cps at 25° C.

11. The packaged product of claim 1 wherein the container has a single opening for dispensing a multiphase composition.

12. The packaged product of claim 1 wherein said dispensed composition has at least 1 weight percent of each phase contained within said partitionless container.

13. The packaged product of claim 1 wherein said opening has a single pump attached thereto.

14. The packaged product of claim 1 wherein each phase has a distinct physical appearance.

15. The packaged product of claim 1 wherein each phase has a distinct color.

16. The packaged product of claim 1 wherein there are only two phases.

17. A method of using a packaged product of an extrudable, multiphase, aqueous lamellar structured and abutting isotropic liquid cleansing composition for cleansing, comprising:

a surfactant selected from the group consisting of amphoteric, zwitterionic, or a mixture thereof;

an anionic surfactant in the concentration range of about 3 to 40 wt. % in each of said lamellar and said isotropic phase;

a lamellar structurant present in each lamellar phase of said liquid composition, selected from the group consisting of fatty acids, fatty esters, trihydroxystearin; wherein said lamellar phase contains about 5% to 70% by weight percent of oil/emollient particles and wherein said isotropic phase contains at least about 3% by weight of surface active material;

each of said lamellar phases having a low shear viscosity value between 80 and 300 K cps at 25° C.; and each of said isotropic phases having a low shear viscosity value between 15 and 100 K cps at 25° C.

* * * * *